(12) United States Patent
Kraus

(10) Patent No.: US 9,675,398 B2
(45) Date of Patent: Jun. 13, 2017

(54) IMPLANT, METHOD AND TOOL FOR KYPHOPLASTY

(75) Inventor: Kilian Kraus, Werneck (DE)

(73) Assignee: TPL Technology Patents Licenses Killian Kraus, Werneck (DE)

( * ) Notice: Subject to any disclaimer, the term of this patent is extended or adjusted under 35 U.S.C. 154(b) by 1066 days.

(21) Appl. No.: 13/449,924

(22) Filed: Apr. 18, 2012

(65) Prior Publication Data

US 2012/0203346 A1  Aug. 9, 2012

Related U.S. Application Data

(63) Continuation of application No. PCT/EP2010/065790, filed on Oct. 20, 2010.

(30) Foreign Application Priority Data

Oct. 20, 2009 (DE) .......................... 10 2009 050 142

(51) Int. Cl.
| | |
|---|---|
| *A61F 2/44* | (2006.01) |
| *A61B 17/88* | (2006.01) |
| *A61B 17/70* | (2006.01) |
| *A61B 17/72* | (2006.01) |

(52) U.S. Cl.
CPC ...... *A61B 17/8858* (2013.01); *A61B 17/7098* (2013.01); *A61B 17/7258* (2013.01)

(58) Field of Classification Search
CPC ............ A61B 17/8858; A61B 17/7258; A61B 17/7266; A61B 17/7275; A61B 17/7097; A61B 17/885; A61B 17/8852; A61F 2/44; A61F 2/442
USPC ...................... 623/17.11–17.16; 604/104–109
See application file for complete search history.

(56) References Cited

U.S. PATENT DOCUMENTS

| | | | | |
|---|---|---|---|---|
| 3,131,809 | A | * | 5/1964 | Rudes ...................... B65D 3/00 206/457 |
| 4,453,539 | A | * | 6/1984 | Raftopoulos et al. .......... 606/63 |
| 5,059,193 | A | * | 10/1991 | Kuslich .......................... 606/247 |
| 2007/0043373 | A1 | * | 2/2007 | Sala et al. ........................ 606/80 |
| 2007/0173939 | A1 | | 7/2007 | Kim et al. |
| 2008/0281364 | A1 | | 11/2008 | Chirico et al. |
| 2009/0171390 | A1 | * | 7/2009 | Sankaran ....................... 606/246 |

(Continued)

FOREIGN PATENT DOCUMENTS

| | | |
|---|---|---|
| WO | 2007/078692 A2 | 7/2007 |
| WO | 2008/137192 A1 | 11/2008 |

OTHER PUBLICATIONS

International Search Report of PCT/EP2010/065790, Dated Feb. 17, 2011.

*Primary Examiner* — Si Ming Ku
(74) *Attorney, Agent, or Firm* — Laurence A. Greenberg; Werner H. Stemer; Ralph E. Locher

(57) ABSTRACT

An implant contains two end pieces disposed coaxially and at an axial distance, a cage, which connects the end pieces, and webs connecting the two end pieces. The two ends of each web are offset from each other by an equal initial angle in an initial state of the implant. The implant can be expanded by rotation of the end pieces in opposite directions about the center longitudinal axis. A tool for the implant has a handle and a main element with a receptacle for the implant and with two rotating devices, which act with a force fit on engaging elements of the implant and can be rotated oppositely in relation to each other.

9 Claims, 10 Drawing Sheets

(56) References Cited

U.S. PATENT DOCUMENTS

2009/0204216 A1\* 8/2009 Biedermann et al. ..... 623/17.12
2010/0145396 A1\* 6/2010 Thornes ............... A61B 17/746
606/313

\* cited by examiner

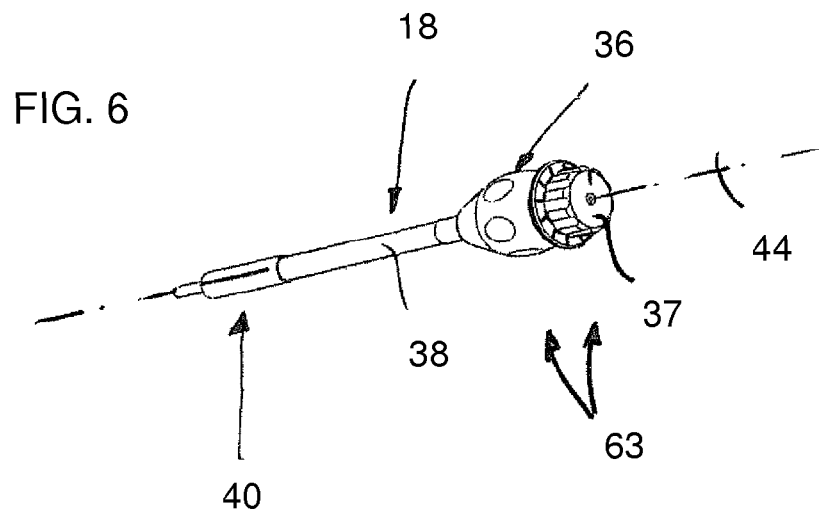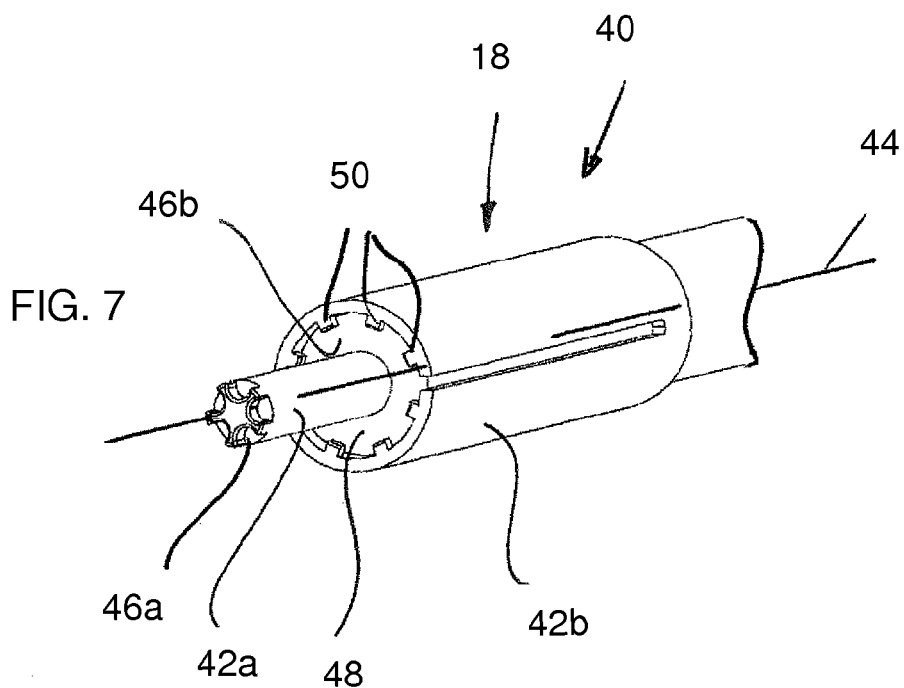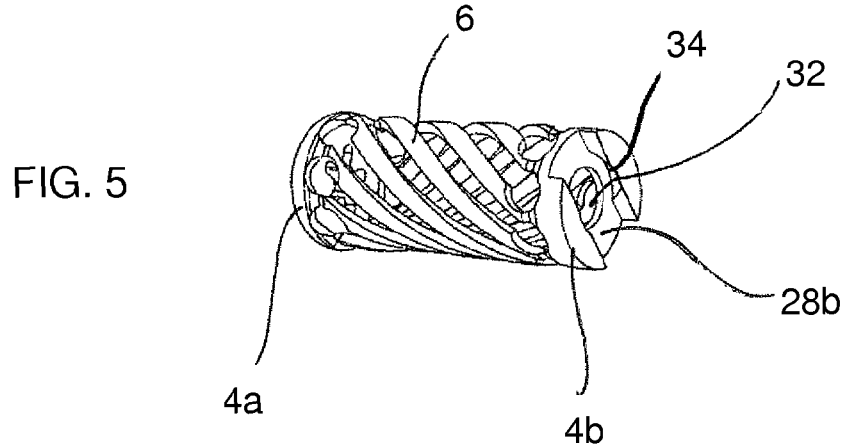

IMPLANT, METHOD AND TOOL FOR KYPHOPLASTY

CROSS-REFERENCE TO RELATED APPLICATION

This is a continuation application, under 35 U.S.C. §120, of copending international application No. PCT/EP2010/065790, filed Oct. 20, 2010, which designated the United States; this application also claims the priority, under 35 U.S.C. §119, of German patent application No. DE 10 2009 050 142.8, filed Oct. 20, 2009; the prior applications are herewith incorporated by reference in their entirety.

BACKGROUND OF THE INVENTION

Field of the Invention

The invention relates to an implant, a method and a tool for kyphoplasty. FIG. 16 illustrates a method designated as kyphoplasty from the prior art. Image A shows a vertebral body 100 of a human spinal column, which vertebral body 100 has collapsed in the axial direction of the spinal column, as is indicated by the line 102. A kyphoplasty method is intended to return the vertebral body 100 to its original shape and stabilize it in the latter.

For this purpose, the vertebral body 100 is provided with at least one bore 104, which extends into the collapsed cancellous bone (spongiosa). According to image B, an inflatable body in the form of a balloon 106 is introduced into the bore 104 with the aid of an operating tool 108. The balloon is empty and is thus located in an initial state.

According to image C, the balloon is filled with pressure liquid 110, whereupon it expands, displaces the spongy bone and straightens the defective vertebra 100 again, such that the surfaces 112 of the latter directed toward respective adjacent vertebrae are oriented approximately as in the original state. The balloon 106 is thus brought to an expansion state in which it experiences an increase in volume. The balloon 106 is returned to its original shape, as shown in image B, by release of the pressure liquid 110, i.e. is transformed again to its initial state, and according to image D removed from the vertebral body 100. The hollow space 112 created in the vertebral body 100 by the inflation of the balloon 106 is then filled with a hardening sealing compound 114.

In another method known from the prior art, a mechanically expandable body is inserted as an implant into a bore extending into the vertebral body. The implant or the expansion body is, in the initial state, a cylindrical part with a central longitudinal axis. The jacket surface of the cylinder is formed by webs connected to one another like a mesh. After it has been placed in the vertebral body, the implant is brought to an expansion state with the aid of an operating tool that matches the implant. For this purpose, the axial length of the expansion body is shortened, i.e. the top and bottom of the cylinder are moved toward each other. In this way, the webs connected to one another like a mesh curve outward to expand in the radial direction. This achieves an effect similar to that of the abovementioned balloon fillable with pressure liquid. However, in contrast to the balloon, the expansion body, i.e. the implant, remains in the expansion state after its transformation, i.e. in the increased volume in the vertebral body. The hollow space receiving the implant is likewise filled with a hardening sealing compound.

A disadvantage of this method is, for example, that it is almost impossible for the expansion body once deformed, i.e. expanded, to be removed again from the vertebral body. However, removal is necessary, for example, if it is found that, despite a maximum increase in volume of the expansion body, the vertebra cannot be satisfactorily straightened. It is true that the known expansion body can be drawn again in length by the operating tool, whereupon its circumference decreases. However, because of the metallic material used (e.g. titanium), complete recovery of the original diameter of the expansion body is no longer achievable. The reason for this is, during the expansion, the plastic deformation of the mesh connecting the top and bottom, i.e. the endpieces, of the implant. Although some of the deformation can be reversed by once again moving the endpieces apart from each other, starting from the expansion state, this cannot be achieved completely. A radially widened implant remains.

The bore in the vertebral body for introduction of the implant should be made as small as possible however, so as not to place a burden on the patient and so as not to further weaken the stability of the vertebral body. In the initial state, the diameter of the implant therefore corresponds to the diameter of the access opening in the vertebral body. The implant, once it has been expanded and then contracted again, can no longer be removed through this opening.

SUMMARY OF THE INVENTION

The object of the invention is to make available an improved implant, method and tool for kyphoplasty.

As regards the implant, the object is achieved by an implant for kyphoplasty. The implant has two endpieces. These are arranged coaxially with respect to a central longitudinal axis of the implant and at an axial distance from each other. The implant also has a cage, which connects the endpieces and concentrically surrounds the central longitudinal axis. The cage contains a plurality of longitudinally extending webs, with each web connecting the two endpieces. The webs are only connected to the endpieces, i.e. not to one another. In other words, the two ends of a web are each respectively connected to one of the endpieces. The implant can be located in an initial state. In this state, the two ends of each web are offset from each other by an equal initial angle in the circumferential direction with respect to the central longitudinal axis. Starting from the initial state, the implant can also be brought to an expansion state. This is done by rotation of the two endpieces in opposite directions about the central longitudinal axis. The rotation takes place in that direction of rotation in which the circumferential positions of the two ends of each web are moved toward each other.

The central longitudinal axis defines a direction of insertion of the implant into a patient. That is to say, this implant is inserted into the patient by axial displacement along the central longitudinal axis. The endpiece facing in the direction of insertion is therefore designated as a front endpiece and is configured, for example, as a dome, hemisphere, spherical cap or similar, in order to be easily insertable into the patient or into a bore provided for the implant. In the non-expanded initial state mentioned above, the webs are therefore arranged such that the whole implant does not exceed a maximum diameter. The implant has, for example, approximately the contour shape of a rectilinear circular cylinder. Therefore, in the initial state, the webs generally run along a jacket surface of the circular cylinder, with the two endpieces forming the top and bottom of the circular cylinder. A respective web then runs along a helical line, i.e. the webs are wound helically. However, it is also conceivable that the implant, in the initial state, has approximately the shape of a barrel or a rotational ellipsoid. The webs then run along the jacket surface thereof. In general, all the webs also have an identical shape and are generally distributed uniformly about the circumference of the central longitudinal axis.

During the expansion, i.e. the transformation from the initial state to the expansion state, the initially circumferentially offset ends of a respective web move toward the same circumferential position. The webs move radially outward. The external diameter of the implant increases. In the state of maximum expansion, the ends of the webs then lie at the same circumferential position, i.e. the web runs approximately in the axial direction. The implant then assumes, for example, approximately the contour shape of a barrel body. The webs themselves are in this case deformed along their entire length or mainly at their connections to the endpieces. The deformation in this case is generally a plastic deformation, such that, after completion of the movement, the implant remains mechanically stable in the expansion state and does not spring back. Depending on how far the endpieces are rotated relative to each other, it is possible to obtain different expansion states and, therefore, different external diameters.

The implant is generally configured in such a way that the transformation from the initial state to the expansion state does not lead to any reduction in the axial length of the implant, and if anything to a slight lengthening. Since the transformation takes place through rotation of the endpieces, a reverse transformation from the expansion state to the initial state is also possible by corresponding rotation of the endpieces in the opposite direction. The implant according to the invention in this respect affords the important advantage that it can be turned back completely to the initial state, that is to say the initial shape, i.e. once again has the maximum initial diameter. This is possible in particular if, in the initial state, a residual gap is present between two adjacent webs, seen in the circumferential direction. The corresponding gaps then likewise run, for example, in a helical line along the jacket surface of the abovementioned rectilinear circular cylinder. During the rotation back to the initial state, the residual gap permits a slight over-rotation beyond the initial state, which exceeds the elastic deformation limit of the implant material, such that the initial state is in fact reached.

According to an advantageous embodiment, in the initial state of the implant, the ends of each web are offset by an initial angle of 180° in the circumferential direction with respect to the central longitudinal axis. In other words, the webs, from one of their ends to the other, surround the half cylinder circumference of the implant. The turn height of a corresponding helical line then corresponds to twice the distance between the two endpieces. With an original offset of this kind, the greatest possible angle of expansion of the implant is achievable, i.e. the greatest possible radial widening of the webs between initial state and expansion state.

In another preferred embodiment of the implant, the ends of a web are weakened in relation to the rest of the web in a manner that favors a deformation. The aim of the transformation is to ensure that as far as possible the webs themselves do not deform. As far as possible, therefore, it is only the areas of the implant where the webs merge into the endpieces that should move. This can be achieved, for example, by an articulated connection of the webs to the endpieces. However, the alternative weakening is generally to be preferred. In other words, the piece connecting the webs to the endpieces is deliberately weakened, in order to achieve there an easy and targeted material deformation of the webs during the rotation of the endpieces in opposite directions. The weakening can also be obtained, for example, by a notch in the webs. Alternatively, the material of the ends of the webs can be weakened, for example, by the fact that the material there is not hardened, or is less hardened, compared to the rest of the web. Thus, a targeted deformation of the implant or of the webs can be achieved at a defined location. Moreover, it is thus possible to ensure that the remaining part of the web has hardly any deformation.

The weakening is preferably achieved by the fact that the cross section of the ends of the webs is narrowed in relation to the cross section of the rest of the web.

In a preferred variant of this embodiment, the webs are narrowed by a recess present on only one side of the web. In this connection, a "side" denotes a circumferentially facing edge area of a web. It is particularly advantageous if the recess is located on that side of the web facing in that direction of rotation of the web end leading to a transformation from the initial state to the expansion state. In other words, the recess is formed on that side of the web facing in the expanding rotation direction. A recess denotes, for example in the case of a web having a rectangular cross section, that the respective three remaining web sides run flush, and only the web side having the recess is set back into the web at the location thereof. The arrangement of the recess on the web side just mentioned has the effect that, in the case of a web having a polygonal cross section, the web edges deploy radially outward in a particularly favorable manner.

In another preferred embodiment, in an axial central area of the implant or of the web, the surface normal of an outwardly directed surface of each web only has a radial component and, if appropriate, an axial component. This applies both to the expansion state and to the initial state. In other words, the webs are not subject to any torsional movement in the central area, i.e. at the axial center of the implant, which is generally also the location of greatest radial widening. Particularly in the case of webs having a polygonal cross section, this prevents a situation where, during expansion, edges of the web turn outward and, for example, scrape against the patient. In other words, in the central area, the outer faces of the webs thus form tangential surfaces to the cylinder jacket or barrel shape of the implant.

In another preferred embodiment, a first endpiece of the implant, preferably the front one in the direction of insertion, has a circumferentially acting first engaging element for a tool. The opposite, second endpiece has a through-opening for the tool, and, in addition, a circumferentially acting second engaging element for the tool. The tool can then pass through the through-opening and the second endpiece and through the interior of the implant to the first endpiece, in order to come into engagement there with the first engaging element. At the same time, the tool also comes into engagement with the second engaging element on the second endpiece. With the aid of the tool, a respective rotation movement or a torque can then be applied to the endpieces, in order to rotate them in opposite directions between initial state and expansion state.

In a variant of this embodiment, the first engaging element is a recess in the first endpiece, and the second engaging element is a form-fit element on the outer circumference of the second endpiece. In other words, the second engaging element then surrounds the through-opening.

In another preferred embodiment, the implant is made in one piece. This makes it possible, for example, to produce the implant from a rod-shaped solid material by turning, drilling and laser cutting.

As regards the method, the object is achieved by a method for kyphoplasty. The method is used for actuating an implant according to the invention. According to the method, starting from the initial state, and in order to expand the implant, the endpieces are rotated in opposite directions about the longitudinal axis in such a way that the circumferential positions of the ends of each web move toward each other. The endpieces are rotated until a desired radial expansion state of the webs is obtained, i.e. an expansion state with desired radial widening. In order to contract the implant, the endpieces are rotated in opposite directions about the central longitudinal axis in such a way that the circumferential positions of the ends of each web move away from each other. This is likewise done until a desired expansion state of reduced diameter or the initial state is reached. The expansion is in this case the procedure of transformation from the initial state to the expansion state, while the contraction describes the correspondingly opposite transformation.

In a preferred embodiment of the method, the endpieces are rotated in opposite directions such that the axial central area of the implant remains at a fixed, e.g. spatially fixed, circumferential position. In other words, a symmetrical movement of the endpieces in opposite directions takes place, such that the central area more or less rests in the circumferential direction and only executes a radial movement. The two endpieces are therefore rotated in opposite directions through the same angle with respect to a spatially fixed reference system. Particularly if the method is performed inside a patient, no circumferential movement of the webs takes place at the central area, and this is particularly gentle on the patient. For example, no scraping effects or the like occur at the location of maximum radial widening of the implant, namely in the central area.

As regards the tool, the object of the invention is achieved by a tool for kyphoplast, which tool is used for operating an implant according to the invention. The tool has a handle and a rod-shaped main body, which has a central longitudinal axis. The handle is arranged on one end of the main body or on a lengthwise end, while a receiver for the implant is generally arranged on the other end. In other words, the implant can therefore be fitted on the end of the main body directed away from the handle. An operator, e.g. a surgeon, can therefore grip the tool by the handle, in order to insert the front end of the main body with the implant into the inside of the patient. The implant can preferably be received on the main body in such a way that the central longitudinal axes of main body and implant coincide. The tool also has two rotation devices, wherein each of the rotation devices acts with a force fit on a respective engaging element of the implant. The rotation devices are oppositely rotatable in both directions with respect to the central longitudinal axis of the main body. Therefore, by actuation of the rotation devices when an implant is fitted, a torque is applied to the engaging element, in order to effect the above-described rotation of the endpieces about the central longitudinal axis and therefore the abovementioned expansion or contraction.

In a preferred embodiment, the rotation devices are rotatable in opposite directions with respect to the handle and are positively guided with respect to an equal angle offset. In other words, with the handle held securely, a movement of the two engaging elements takes place which is contradirectional and synchronous with respect to the angle offset. In this way in particular, the abovementioned embodiment of the implant operation is possible in which the central area remains stationary and only the endpieces rotate in opposite directions through the same angle. This has the result that the central area then also remains stationary with respect to the handle.

In a preferred embodiment, the tool has at least one actuation element that drives one or preferably two rotation devices. Such an actuation element is preferably arranged in proximity to the handle or directly on the handle.

In a variant of this embodiment, the actuation element is a rotary knob that can rotate about a rotation axis extending transversely with respect to the central longitudinal axis of the tool. This embodiment also favors the immobilization of the handle in a defined circumferential position, and the above-described transformation of the implant with stationary central area.

Other features which are considered as characteristic for the invention are set forth in the appended claims.

Although the invention is illustrated and described herein as embodied in an implant, a method and a tool for kyphoplasty, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 5 is a perspective view of the implant according to FIG. 1 with an alternative engaging element;

FIG. 6 is a perspective view of the tool from FIG. 3;

FIG. 7 is a perspective view of the tool from FIG. 3 without the implant;

DETAILED DESCRIPTION OF THE INVENTION

Figure 1:
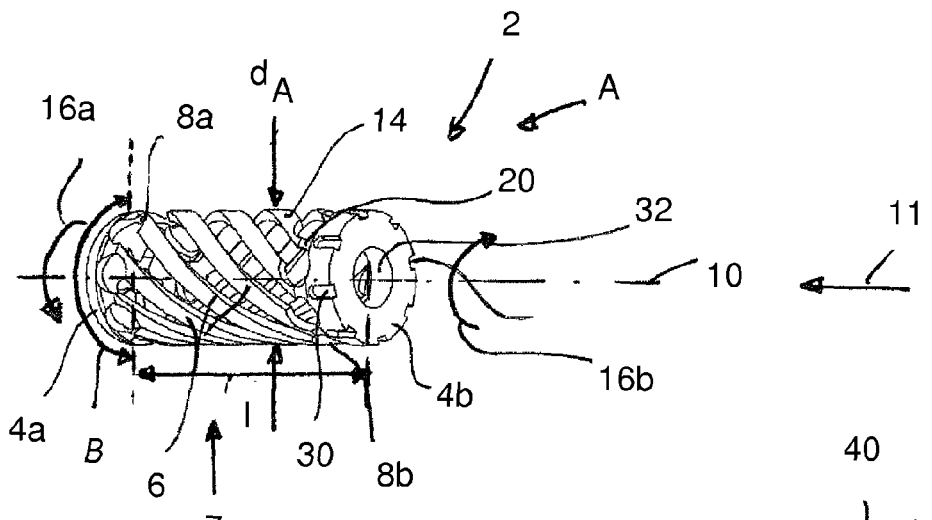
FIG. 1 is a diagrammatic, perspective view of an implant according to the invention in an initial state.

Referring now to the figures of the drawing in detail and first, particularly, to FIG. 1 thereof, there is shown an implant 2 according to the invention in an initial state A. The implant has substantially the shape of a rectilinear circular cylinder. A bottom and top of the circular cylinder are formed by a first endpiece 4a and a second endpiece 4b. A jacket surface of the cylinder is formed by a plurality of webs 6, which together form a cage 7. These wind in the form of helical lines on the cylinder jacket from the endpiece 4a to the endpiece 4b. The ends 8a, 8b of each web 6 are connected to the endpieces 4a, 4b. The implant has a central longitudinal axis 10. In other words, the endpieces 4a, 4b are thus connected to each other via the helically wound webs 6. In the unexpanded initial state A, the webs run in parallel at each location, in such a way that their respective tangents run parallel at the same axial height. Each web 6, with corresponding rotation about the central longitudinal axis 10, is thus conceived as merging into another web 6.

In the initial state A, the implant has a radial extent that does not exceed a maximum diameter $d_A$. The implant is intended to be inserted into a patient along the central longitudinal axis 10 in the direction of arrow 11. Therefore, the first endpiece 4a is a front endpiece and is configured approximately as a spherical cap.

In the example, the webs 6 are distributed uniformly about the circumference of the implant 2 and are each at the same distances from one another. Thus, between every two webs 6, there is a residual gap 12, which likewise has the shape of a helical line. The distance between the webs 6, i.e. the width of the residual gap 12 in the circumferential direction, is smaller than the corresponding width of the webs 6. The webs 6 are thus arranged such that their outer faces 14 are part of a common cylindrical envelope surface.

Figure 2:
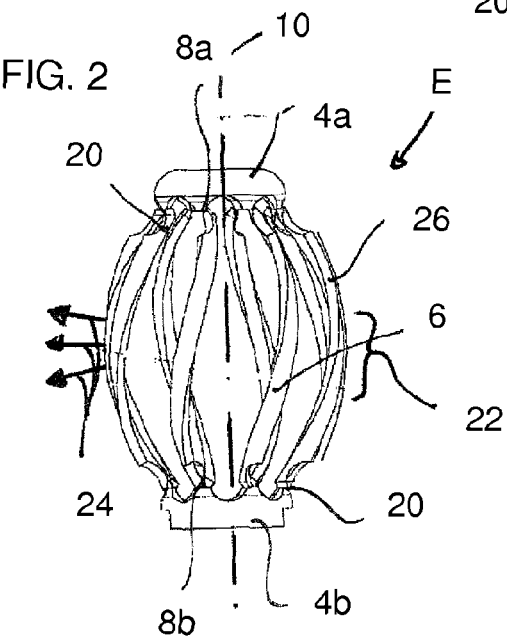
FIG. 2 is a side view of the implant from FIG. 1 in an expansion state.

FIG. 2 shows the implant from FIG. 1 in an expansion state E. In contrast to the prior art, the increase in volume of the implant 2 in relation to the initial state A is not achieved by shortening the length of the implant 2, i.e. reducing the axial length I between the endpieces 4a, 4b. The transformation to the expansion state E is achieved by the fact that the two endpieces 4a, 4b are twisted relative to each other in such a way that the ends 8a, 8b of the webs 6 move toward each other with respect to the circumferential direction of the central longitudinal axis 10. During the expansion, the rotation of the endpieces 4a, 4b thus takes place in the direction of the arrows 16a, 16b. In the expansion state, the diameter $d_E$ of the implant reaches a maximum.

Figure 3:
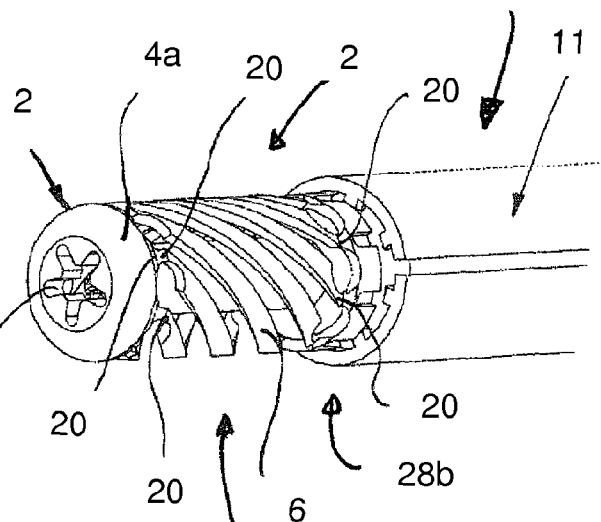
FIG. 3 is a perspective view of implant from FIG. 1 when fitted onto a tool.

The corresponding rotation or the required torque is produced by a tool 18 which is shown in FIG. 3 and onto which the implant 2 is fitted. However, FIG. 3 shows a situation in which the implant 2 is not yet fully fitted. The tool 18 thus causes the mutual rotation of the endpieces 4a, 4b about the central longitudinal axis 10. The endpieces 4a, 4b are thus maintained at a constant distance of the length I. The webs 6 curve radially outward and bring about the desired increase in volume. In other words, the implant in the expansion state E encloses a greater spatial volume than in the initial state A.

In FIG. 1, the ends 8a, 8b of each web 6 on the endpieces 4a, 4b are offset from each other by an initial angle β of 180° in the circumferential direction. The maximum expansion between initial state A and expansion state E according to FIG. 2 is then achieved upon a relative rotation of the endpieces 4a, 4b through 180° in the direction of the arrows 16a, 16b in relation to the situation in FIG. 1. In FIG. 2, therefore, the ends 8a, 8b of each web 6 lie at the same circumferential position, i.e. their angle offset is then 0°.

In the side view of the implant 2 according to FIG. 2, the webs 6 thus extend rectilinearly, i.e. parallel to the central longitudinal axis 10, from one end 8a to their other end 8b.

At their ends 8a,b, the webs 6 have weakened locations 20, which act like joints. The weakened locations 20 mean that, when the endpieces 4a, 4b are twisted in opposite directions, the ends 8a, 8b of the webs can twist in relation to the endpieces 4a, 4b. The weakened locations 20 are configured in such a way that, during a twisting of the endpieces 4a, 4b, the web areas extending between two weakened locations 20 of one web 6 do not twist, or at least twist only slightly, such that the webs 6 substantially retain their original shape. The deformation of the weakened locations 20 also takes place uniformly, such that the orientation of the outer faces 14 in an axial central area 22 of the implant 2 is almost unchanged between initial state A and expansion state E. Therefore, a normal vector in the form of the surface normals 24 of the outer face 14 in the central area 22 only has a radial component and axial component, and no components in the circumferential direction.

In the expansion state E, the outer faces of the implant 2 form approximately part of the envelope surface of a barrel-shaped body. It is thus ensured that, when the endpieces 4a, 4b are twisted in opposite directions, the webs 6, at least in the central area 22, bear with their outer face on a large surface of the surrounding spongy bone and are able to displace the latter to the side. This also prevents the webs 6 from scraping off spongy tissue via sharp edges in the form of rims 26. This could in fact happen, for example, if the webs 6 themselves twisted and, therefore, their edges 26 would thus exert a scraping action on the spongy bone.

In order to ensure the described orientation of the webs 6 during the expansion of the implant 2, the weakened locations 20 are formed from two differently shaped parts. The first part is formed by a reduced wall thickness of the web in the radial direction, and the second part is formed by a reduced width of the webs 6 in the circumferential direction.

The two endpieces 4a, 4b are configured such that they can be brought into form-fit engagement with the tool 18 and, with the aid of the latter, can be twisted relative to each other. For this purpose, the first endpiece 4a has a central recess with a shape deviating from the circular shape, for example an approximately star-shaped recess, which represents a first engaging element 28a acting in the circumferential direction.

Figure 4:
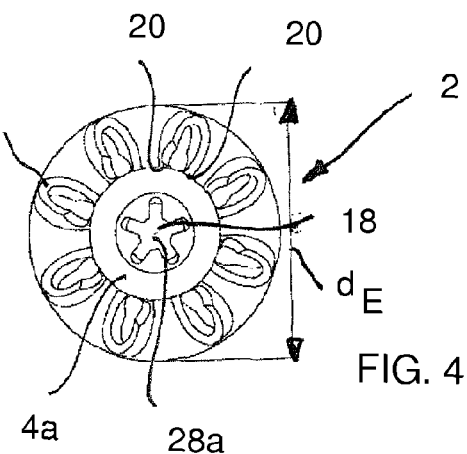
FIG. 4 is a front view of the implant from FIG. 1.

FIG. 4 shows a plan view of the implant 2 from the front, illustrating the engaging element 28a and, engaging therein with a form fit, the tool 18.

The rear endpiece 4b is configured such that the operating tool 18 can engage on the outer circumference or the outer end face of the endpiece 4b with a form fit acting in the direction of rotation. For this purpose, the endpiece 4b has an engaging element 28b. The latter is designed as a form-fit element 30 by axially extending slit-shaped recesses. In an alternative (not shown), the endpiece 4b could also be configured corresponding to the endpiece 4a and have a corresponding recess.

In the example, however, an additional circular through-opening 32 is provided, which does not permit a form fit and through which a part of the tool 18 can reach the engaging element 28a.

FIG. 5 shows an alternative engaging element 28b in the form of a transverse groove on the endpiece 4b. The alternative engaging element 28b is also configured in such a way that a form fit acting in the axial direction can also be established with the tool 18. An undercut 34 is provided for this purpose.

According to FIG. 6, the tool 18 has a handle 36 and an elongate main body 38 mounted on the latter. Opposite the handle 36, it has an actuation end 40. The implant 2 can be fitted on there (see FIG. 3). The actuation end thus also forms a receiver 41 for the implant.

According to FIG. 7, the actuation end 40 has a first portion 42a and a second portion 42b, which are arranged mutually coaxially with respect to a central longitudinal axis 44 and are rotatable relative to each other.

The first portion 42a has a smaller diameter than the second portion 42b and has, on its front face, a shaped piece which complements the engaging element 28a and which forms a first rotation device 46a. Its access to the engaging element 28a is obtained by guiding the portion 42a through the through-opening 32. The front face 48 of the second portion 42b directed toward the first portion 42a is configured in the form of a rotation device 46b, which permits a rotationally acting form fit with the engaging element 28b. For this purpose, an axial recess receiving the endpiece 4b is provided with radially inwardly extending projections 50, which engage in the slit-shaped recesses 30. In the tool, one rotation device 46a is, for example, connected to a knurled wheel 37 at the front, while the other rotation device is connected to the handle for rotation therewith. By respective rotation of handle 36 and knurled wheel 37, the rotation device 46a, 46b can then be individually actuated. Handle 36 and knurled wheel 37 thus represent actuation elements 63 for the rotation device 46a, 46b.

Figure 8:
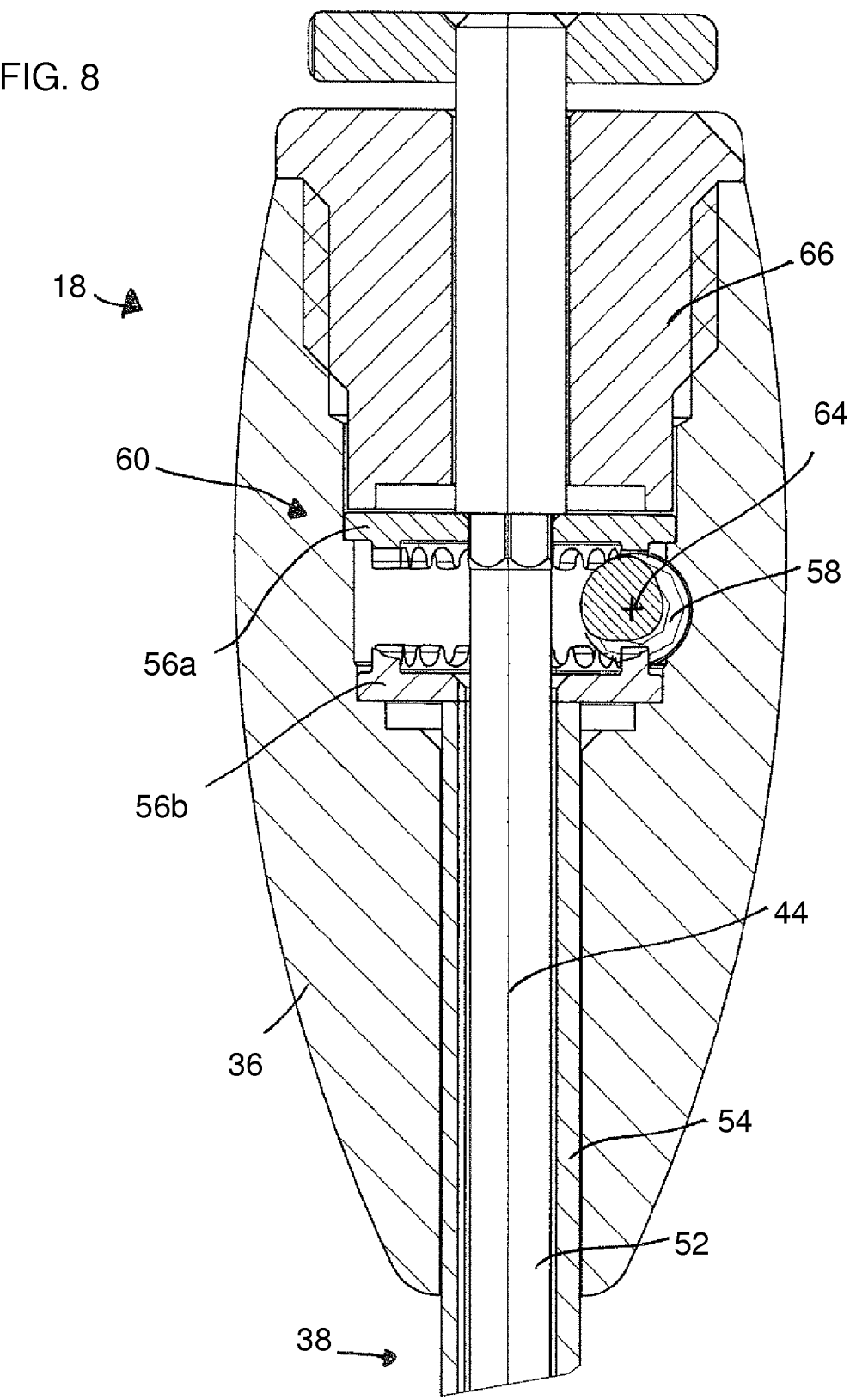
FIG. 8 is a cross-sectional view of an alternative tool.

In a preferred variant according to FIG. 8, the tool 18 is configured such that the portions 42a, 42b can be rotated in opposite directions with respect to the handle 36, the rotation always taking place synchronously and in a positively guided manner about the same angle offset.

For this purpose, the portion 42a is connected for conjoint rotation to an inner spindle 52, and the portion 42b to a tube 54 coaxially surrounding the inner spindle 52, which together form the main body 38. In the interior of the handle 36, the inner spindle 52 is mounted, again for conjoint rotation, on a toothed wheel 56a, and the tube 54 on a toothed wheel 56b. These are together coupled to a worm 58 to form a contradirectional worm gear 60. The inner spindle 52 and tube 54 are rotatable in the handle 36 about the central longitudinal axis 44, and the worm 58 is arranged fixed in rotation with respect to the latter. However, the worm is mounted rotatably about a rotation axis 64 perpendicular to the central longitudinal axis 44. The worm gear 60 is held in the handle 36 by a securing nut 66. When the latter is removed, the whole tool 18 can be dismantled, cleaned and sterilized.

Figure 9:
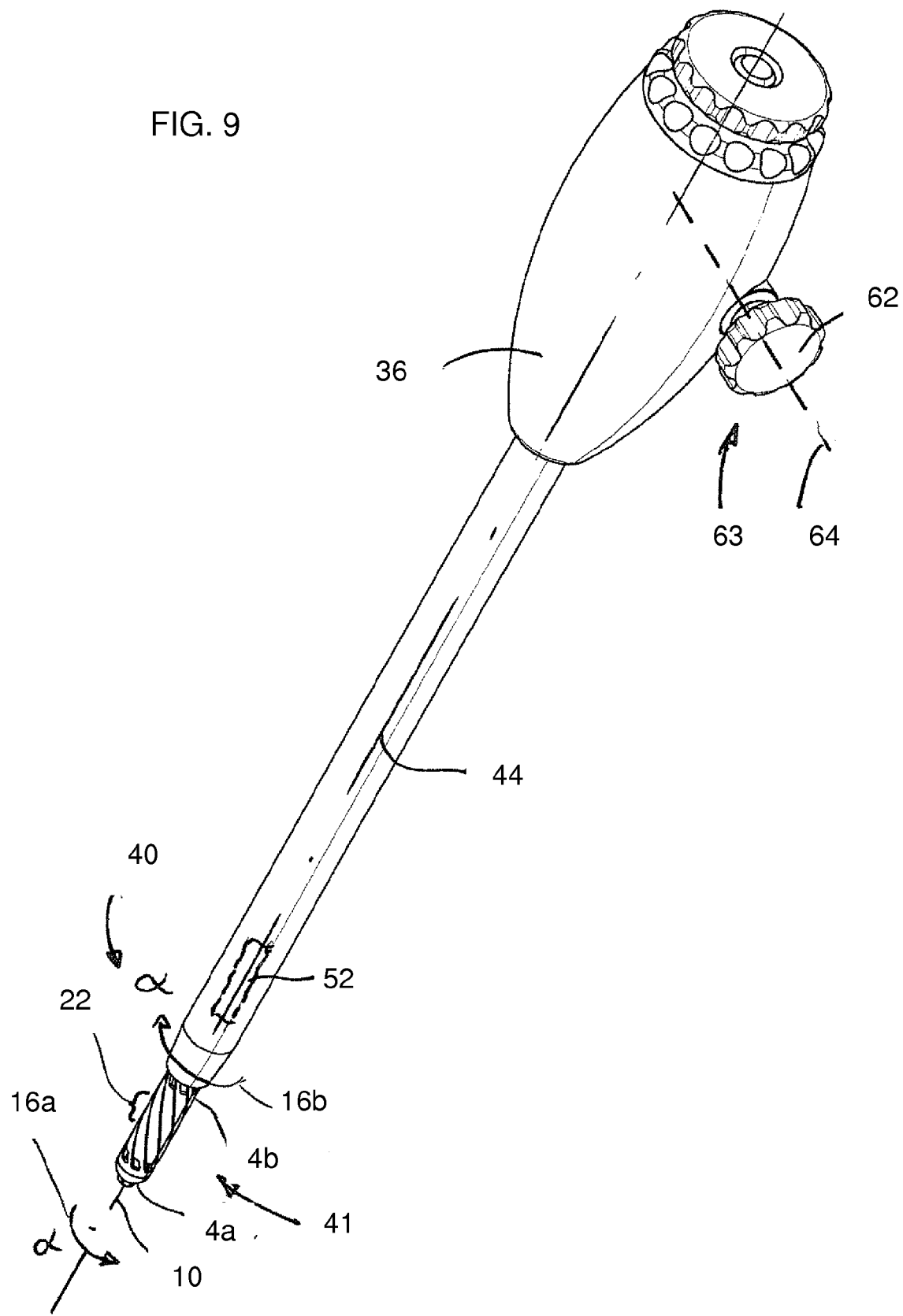
FIG. 9 is a perspective view of the tool from FIG. 8 with the alternative implant.

FIG. 9 shows the external view of the tool 18, with a rotary knob 62 connected to the worm. An alternative implant 2 (see below) is attached and is located with its engaging elements 28a, 28b in form-fit engagement with the rotation device 46a, 46b. If the handle 36 is now held secure and the rotary knob 62 is turned about the rotation axis 64, the inner spindle 52 and with it the endpiece 4a move in the direction of the arrow 16a about the coincident central longitudinal axes 10 and 44 through a defined rotation angle α. At the same time, and in the opposite direction about the same rotation angle α, the tube 54 and the endpiece 4b turn in the direction of the arrow 16b. This strictly contradirectional rotation has the effect that, in relation to the handle 36, the central area 22 hardly moves at all in the circumferential direction and instead only expands radially. Therefore, if the handle 36 is not rotated with respect to a patient (not shown), the central area 22 also experiences no rotation within the patient, but only a radial expansion without scraping action. In this illustrative embodiment, only the rotary knob 62, not the handle 36, is an actuation element 63 for the rotation device 46a, 46b.

Figure 10:
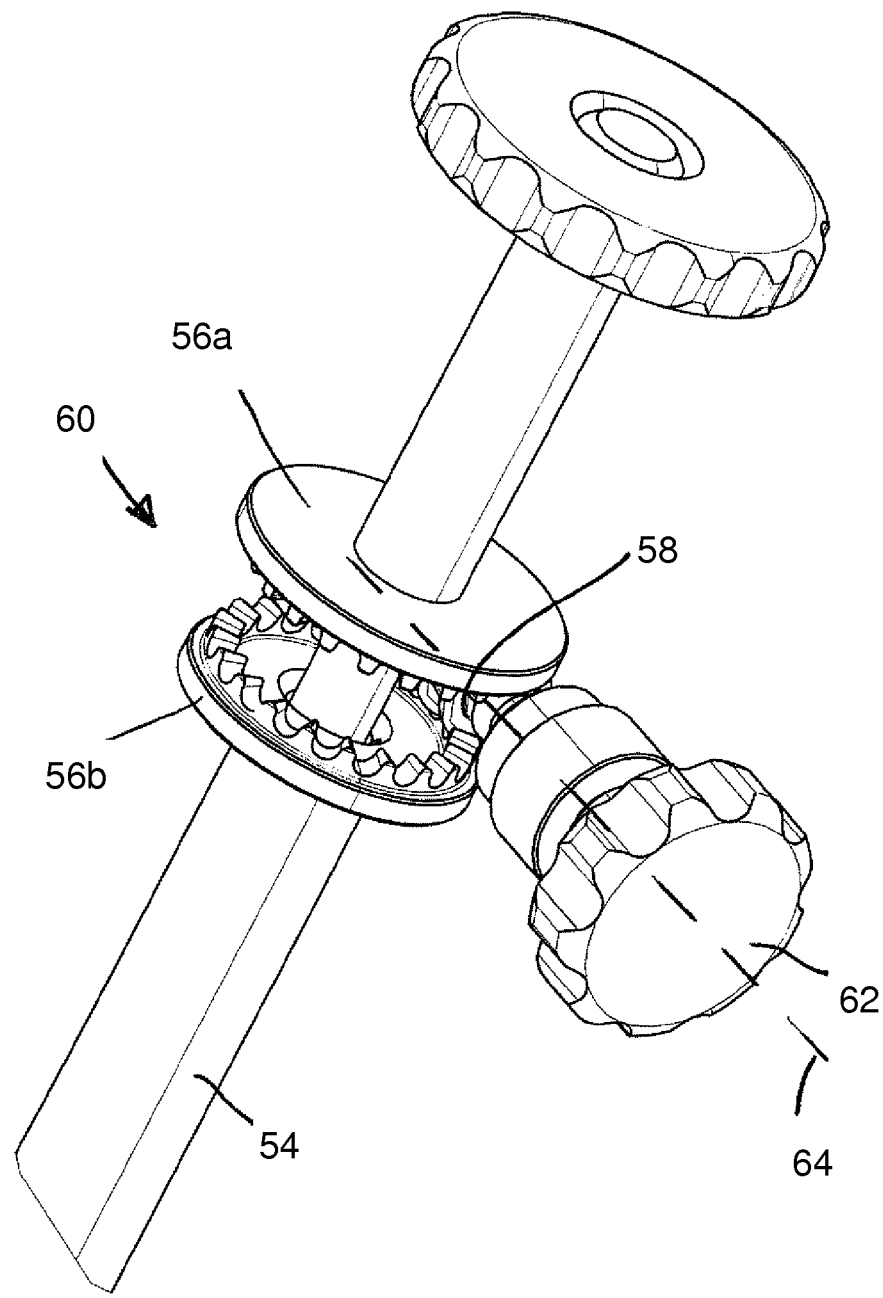
FIG. 10 is a perspective view of the tool from FIG. 8 without a handle.

FIG. 10 shows once again the kinematic relationships between the rotary knob 62 and the worm gear 60, with omission of the handle 36.

Figure 11:
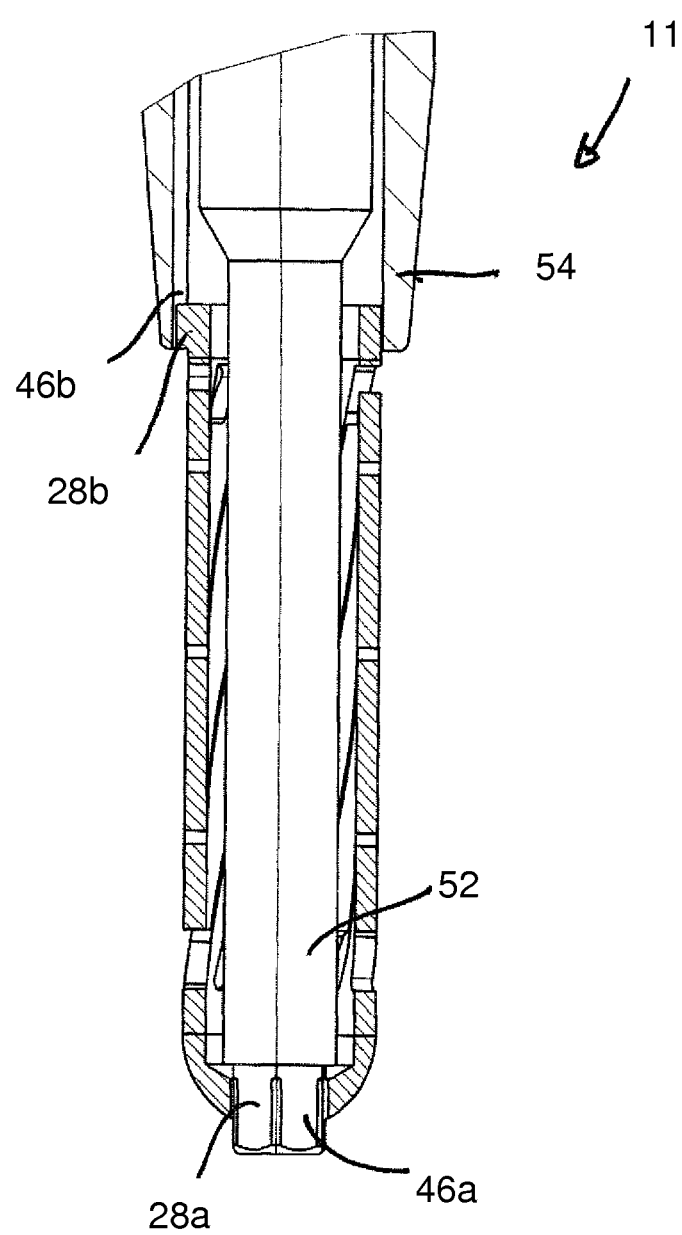
FIG. 11 is a sectional view of the tool from FIG. 8 in detail with the implant.

FIG. 11 shows in detail the actuation end 40 of the tool 18, particularly the engagement of the rotation device 46a on the inner spindle 52 into the engaging element 28a, and the engagement of the rotation device 46b on the tube 54 into the engaging element 28b.

Figure 12:
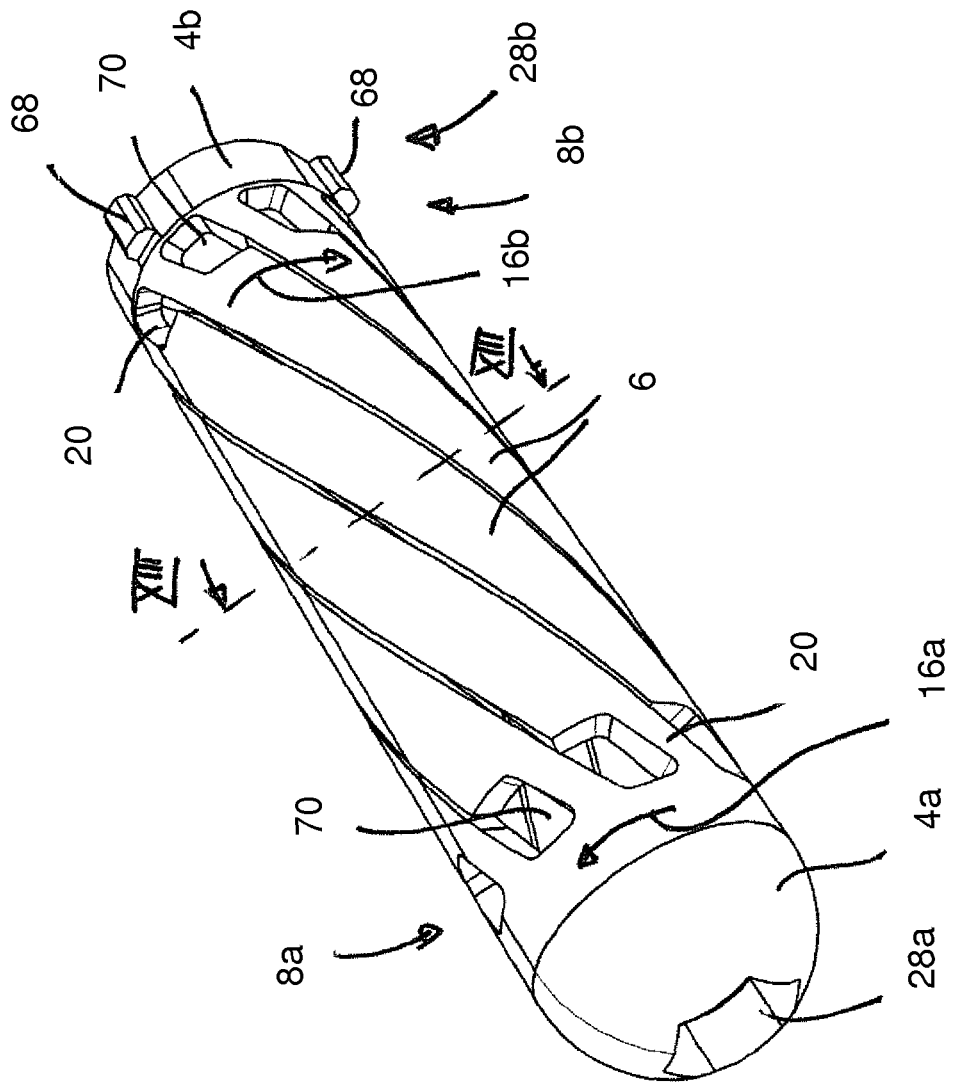
FIG. 12 is a perspective view of the alternative implant from FIG. 8.

FIGS. 9 and 11 already show an alternative implant 2 according to FIG. 12. This differs from the previous embodiment particularly in terms of the configuration of the engaging element 28b in the form of radially outwardly protruding lugs distributed about the circumference and acting as form-fit element 30, and in terms of the engaging element 28a configured in a hexagonal shape. Moreover, at their ends 8a, 8b, the webs 6 have alternatively configured weakened locations 20. In contrast to the first illustrative embodiment, the radial wall thickness of the webs 6 is not weakened, i.e. is even generally maintained in full at the weakened locations 20. Moreover, instead of two lateral recesses, as seen in the circumferential direction, a corresponding recess is formed only on one side of the webs 6 in order to produce the weakened location 20. The side of the webs 6 lying opposite the weakened location 20, and the radial inner and outer surfaces of the webs, are thus substantially flush. Moreover, the corresponding recesses 70 are each formed in that side of the webs 6 pointing in the direction of rotation of the endpiece 4a, 4b in question, that is to say in the direction of the arrows 16a and 16b. The direction of winding of the webs 6 is also counter to that of the first illustrative embodiment, for which reason the arrows 16a, 16b also point in opposite directions.

Figure 13:
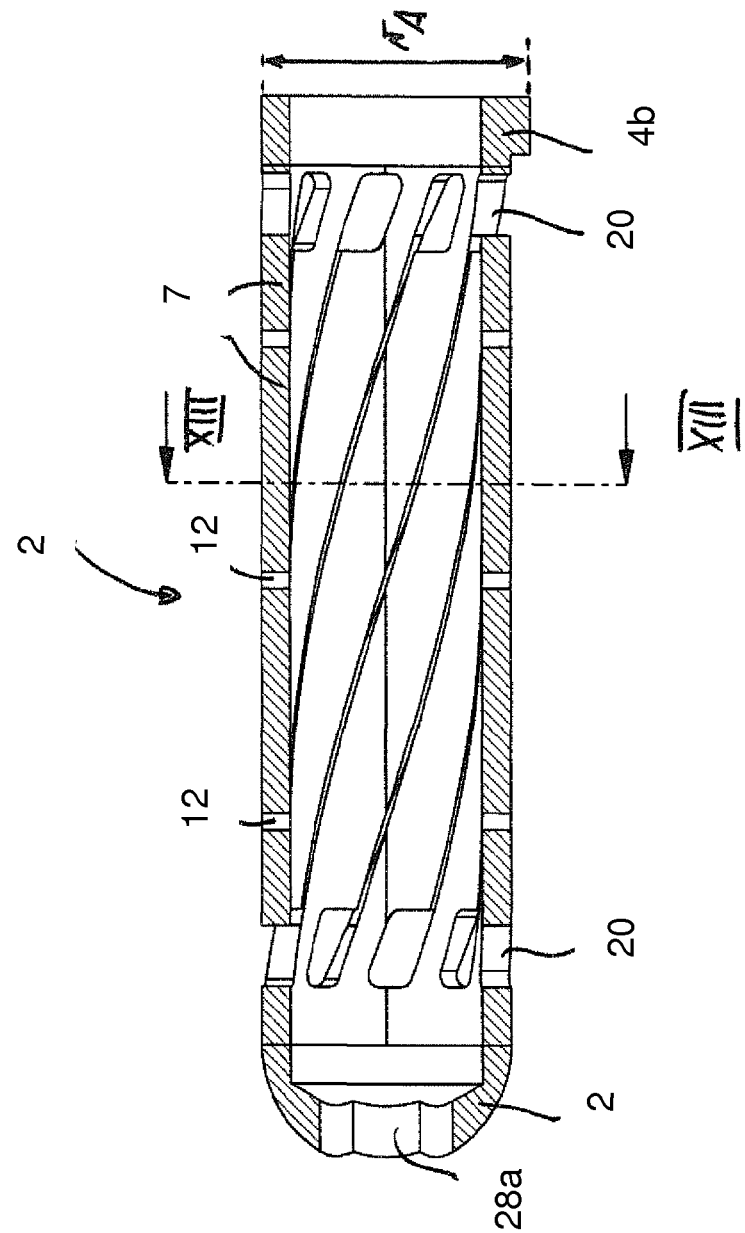
FIG. 13 is a cross-sectional view of the implant from FIG. 8.
Figure 14:
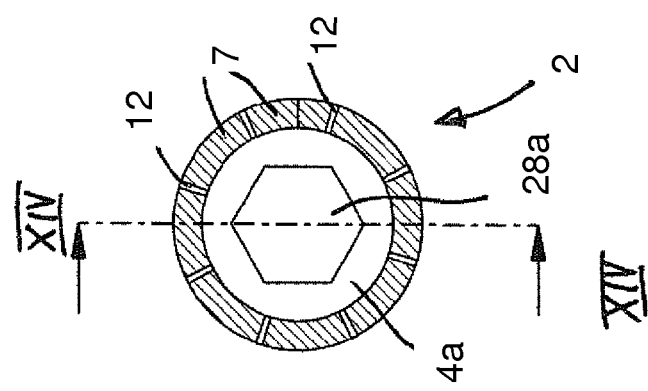
FIG. 14 is a longitudinal sectional view of the implant from FIG. 8.
Figure 15:
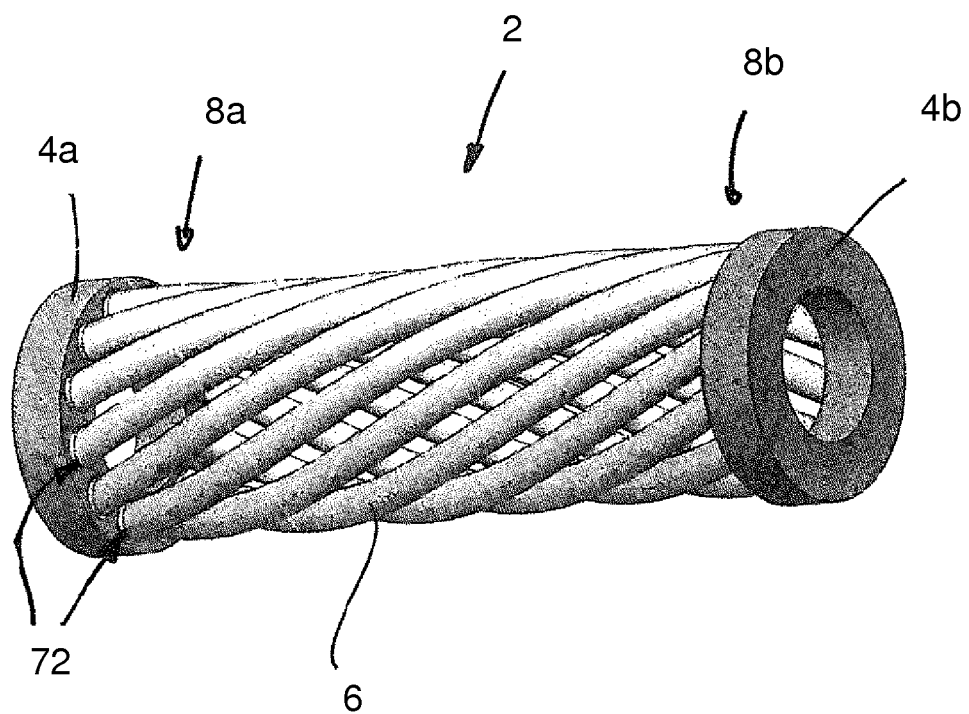
FIG. 15 is a perspective view of the alternative implant with joints and round webs.
Figure 16:
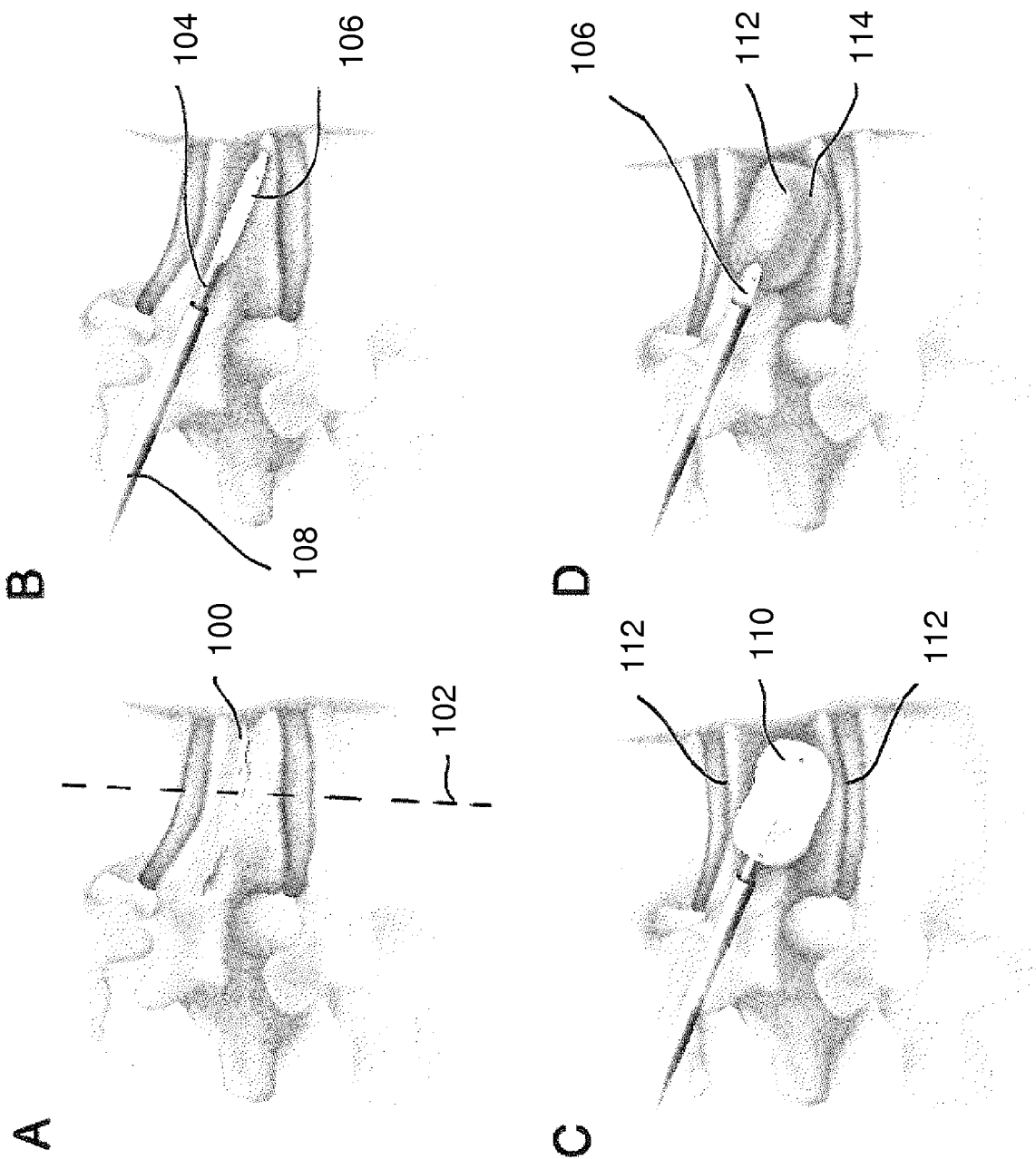
FIG. 16 is an illustration for showing a kyphoplasty method according to the prior art.

FIG. 13 shows a sectional view of the implant 2 from FIG. 12 in the direction of the arrow 13, while FIG. 14 shows a longitudinal section through the corresponding implant 2, which, compared to the first embodiment, shows in particular the absence of weakening in terms of the wall thickness of the webs 7 and of the endpieces 4a, 4b at the weakened locations 20.

It will also be seen from FIG. 14 how the implant 2 can be produced in one piece for example, by it being made from a corresponding rod-shaped solid material that first of all has a central bore drilled through it from the direction of the endpiece 4b, after which the endpiece 4a is milled at the front to give a hemispherical shape, and then the engaging element 28a and the residual gaps 12 and the weakened locations 20 are removed from the solid material, for example by laser cutting.

FIG. 14 shows another alternative implant 2 in schematic form. For simplicity, the engaging elements 28a, 28b have been omitted. An articulated connection between the webs 6 and the endpieces 4a, 4b can also be achieved here if, instead of weakened locations 20 that act like joints, actual joints 72, also called fixing points, are provided in the area of the ends 8a, 8b of the webs 6. The joints can be configured, for example, as ball joints, in which the end 8a, 8b of a web 6 carries a joint ball, which are held in a joint socket in the endpieces 4a, 4b. Moreover, the webs do not necessarily have to be polygonal in cross section, as has been described above. As is shown here, the webs 6 can also be configured as bars, for example of circular cross section.

The invention claimed is:
1. An implant for kyphoplasty, the implant comprising:
two endpieces disposed coaxially with respect to a central longitudinal axis and at an axial distance from each other; and a cage connecting said endpieces and concentrically surrounding the central longitudinal axis, said cage containing a plurality of webs connecting said two endpieces, said webs each having two ends, in an initial state of the implant, being offset from each other by an equal initial angle in a circumferential direction with respect to the central longitudinal axis, the implant being brought to an expansion state by rotation of said two endpieces in opposite directions about the central longitudinal axis, during which rotation circumferential positions of said two ends of each of said webs move toward each other, in the expansion state said webs being plastically deformed and the implant remains mechanically stable in the expansion state and does not spring back.

2. The implant according to claim 1, wherein, in the initial state, said ends of each of said webs are offset by the initial angle of 180° in the circumferential direction with respect to the central longitudinal axis.

3. The implant according to claim 1, wherein said ends of said webs are weakened in relation to a rest of said webs in a manner that favors a deformation.

4. The implant according to claim 3, wherein a cross section of said ends of said webs is narrowed in relation to a cross section of a rest of said web.

5. The implant according to claim 4, wherein said cross section of said ends of said webs is narrowed by a recess present on one side of said webs.

6. The implant according to claim 1, wherein, in an axial central area, a surface normal of a radially outwardly directed surface of each of said webs only has a radial component and an axial component.

7. An implant for kyphoplasty, the implant comprising:
two endpieces disposed coaxially with respect to a central longitudinal axis and at an axial distance from each other; and
a cage connecting said endpieces and concentrically surrounding the central longitudinal axis, said cage containing a plurality of webs connecting said two endpieces, said webs each having two ends, in an initial state of the implant, being offset from each other by an equal initial angle in a circumferential direction with respect to the central longitudinal axis, the implant being brought to an expansion state by rotation of said two endpieces in opposite directions about the central longitudinal axis, during which rotation circumferential positions of said two ends of each of said webs move toward each other, said two endpieces including a first endpiece having a circumferentially acting first engaging element, and a second endpiece having a through-opening formed therein and a circumferentially acting second engaging element for a tool.

8. The implant according to claim 7, wherein said first engaging element is a recess formed in said first endpiece, and said second engaging element is a form-fit element on an outer circumference of said second endpiece.

9. The implant according to claim 1, wherein the implant is made in one piece.

* * * * *